US00PP25440P3

(12) United States Plant Patent
Roberts

(10) Patent No.: US PP25,440 P3
(45) Date of Patent: Apr. 14, 2015

(54) MINT PLANT 'CANYON MINT'

(50) Latin Name: *Mentha piperita*
Varietal Denomination: Canyon Mint

(71) Applicant: Essex Laboratories, Inc., Napavine, WA (US)

(72) Inventor: Donald D. Roberts, Independence, OR (US)

(73) Assignee: Essex Laboratories, Inc., Napavine, WA (US)

( * ) Notice: Subject to any disclaimer, the term of this patent is extended or adjusted under 35 U.S.C. 154(b) by 138 days.

(21) Appl. No.: 13/815,164

(22) Filed: Feb. 4, 2013

(65) Prior Publication Data

US 2014/0223625 P1 Aug. 7, 2014

(51) Int. Cl.
*A01H 5/00* (2006.01)

(52) U.S. Cl.
USPC ..... Plt./259

(58) Field of Classification Search
USPC ..... Plt./259
See application file for complete search history.

(56) References Cited

U.S. PATENT DOCUMENTS

PP11,788 P2 2/2001 Roberts
PP13,720 P2 4/2003 Roberts

OTHER PUBLICATIONS

Burbott, Alice J., et al., "Effects of Light and Temperature on the Monoterpenes of Peppermint," Plant Physiol., 1967, 42 , pp. 20-28.
Fuchs, Sabine, et al., "Biosynthesis of Menthofuran in *Mentha×piperita*; Stereoselective and Mechanistic Studies"; j. Agric. Food Chem., 1999, 47 (10), pp. 4100-4105.
Mahmoud, Soheil S., et al., "Methofuran regulates essential oil biosynthesis in peppermint by controlling a downstream monoterpene reductase," Proc. Natl. Acad. Sci, USA, 2003, Nov. 25; 100 (24) 14481-8.
Rohloff, Jens, et al., Effect of Harvest Time and Drying Method on Biomass Production, Essential Oil Yield, and Quality of Peppermint (*Mentha piperita* L.); J. Agric. Food Chem., 2005, 53 (10), pp. 4143-4148.
Rohloff, Jens, Monoterpene Composition of Essential Oil from Peppermint (*Mentha piperita* L.) with Regard to Leaf Position Using Solid-Phase Microextraction and Gas Chromatography/Mass Spectrometry Analysis; J. Agric. Food Chem.; 1999, 47(9), pp. 3782-3786.

*Primary Examiner* — Annette Para
(74) *Attorney, Agent, or Firm* — Marger Johnson & McCollom, PC

(57) ABSTRACT

Mint selection 05-19-1 denominated 'Canyon Mint' is a new *Mentha piperita* cultivar that produces an essential oil different in composition and has a compact plant type and resistance to mint rust (*Puccinia menthae*) and mint wilt (*Verticillium dahliae*).

3 Drawing Sheets

Latin name of the genus and species: *Mentha piperita.*
Variety denomination: 'CANYON MINT'.

FEDERAL SPONSORSHIP

None

TYPE OF PLANT AND NAME OF VARIETY

The present invention relates to a new and distinct variety of peppermint plant developed from a parent of the species *Mentha piperita* L. The new variety will be identified as 'Canyon Mint.'

BACKGROUND OF INVENTION

This new peppermint was developed in a polycross mint breeding program in which the primary objective was to develop a Mitcham type peppermint variety having a specific oil composition, acceptable yield and resistant to diseases mint wilt and mint rust. Mint wilt is caused by a soil-borne fungus, *Verticillium dahliae* and mint rust is a leaf infection caused by the air-borne fungus *Puccinia menthae*. Only seedlings with no symptoms of mint wilt or rust were selected for further evaluation. 'Canyon Mint' was vegetatively propagated by tip cuttings to increase the selection to 20 plants for continued evaluation in 2006. The selection was again vegetatively propagated this time with stolon sections to over 300 plants for planting and evaluation in 2007. When compared to 'Black Mitcham' as a control, 'Canyon Mint' had less (or no) symptoms of mint wilt than the control and had no mint rust infection. Yield of 'Canyon Mint' is equivalent to 'Black Mitcham' in test plots as a single plant and as multiple plants in larger plots.

DISCOVERY AND ASEXUAL REPRODUCTION

'Canyon Mint' originated as a seedling from an open pollinated polyploid 'Black Mitcham' seedling parent. Diploid 'Black Mitcham' peppermint is sterile and only becomes fertile in the polyploidy state. The 'Black Mitcham' seedling parent to 'Canyon Mint' was one of several mint lines in a polycross breeding system composed of selected male and female fertile polyploid genotypes.

'Canyon Mint' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The inventor has conducted asexual propagation of 'Canyon Mint' for greenhouse and field planting in Monmouth, Oreg., each year since 2005 and the genotype comes true to form with each generation.

SUMMARY OF THE INVENTION

Mint selection 05-19-1 denominated 'Canyon Mint' is a new *Mentha piperita* cultivar that produces an essential oil different in composition than commercially grown mint varieties. The essential oil is similar to standard mint oil in components composition but differs in the typical ratio of components. Organoleptically, it differs from typical peppermint oil. It is resistant to mint rust and more resistant to *Verticillium dahliae* mint wilt than current commercially grown varieties.

BRIEF DESCRIPTION OF THE FIGURES

The accompanying color figures show typical greenhouse and field grown vegetative growth of 'Canyon Mint' and depicts the color as nearly true as reasonably possible.

FIG. 1 is a one year old greenhouse grown plant that illustrates the flowering pattern and multiple flowering shoots of my new mint plant in accordance with the present invention.

FIG. 2 illustrates the shape of the flower collected from a one year old field grown plant.

FIG. 3 illustrates the shape of the leaf and compact growth of one year old 'Canyon Mint' grown under field conditions.

DESCRIPTION OF PLANT

My new mint plant improves upon and is distinct from other mint plants in several characteristics, including but not limited to, the following:

1. The ability to produce an essential oil different in composition but with similar components as 'Black Mitcham' peppermint;
2. A more compact plant but with a branching pattern similar to its parent;
3. An early spring growth similar to 'Black Mitcham' peppermint but with an earlier maturity for desirable chemical composition of its essential oil;
4. A level of resistance to mint wilt (*Verticillium dahliae*) equal to or greater than that of its parent;
5. Resistance to mint rust caused by *Puccinia menthae.*

The essential oil extracted from 'Canyon Mint' has the same components as that of commercial oil produced by 'Black Mitcham' peppermint as illustrated in Table 1. However, the ratio of oil components differs between the commercial peppermint oil and that of 'Canyon Mint'. The concentration of menthone and menthol in the oil of 'Canyon Mint' is lower than that of 'Black Mitcham.' The amount of Menthofuran and Menthyl Acetate in the oil of 'Canyon Mint' is higher than that of 'Black Mitcham.' Organoleptically, the oil of 'Canyon Mint' is different from that of 'Black Mitcham,' reflecting the difference in oil component ratios.

TABLE 1

Composition of 'Canyon Mint' Oil from Test Plots Compared to commercial 'Black Mitcham' Peppermint Oil and Oil from 'Black Mitcham' Peppermint Grown in Test Plots located near Monmouth, Oregon.

| Essential Oil Components | Commercial 'Black Mitcham' 1/ | 2005 Test Plot 'Black Mitcham' 2/ | 2005 Test Plot 'Canyon Mint' 3/ |
|---|---|---|---|
| α-pinene | 0.82 | 0.80 | 0.84 |
| β-pinene | 1.06 | 1.03 | 1.17 |
| 1-limonene | 1.78 | 1.73 | 2.24 |
| 1,8-cineole | 5.33 | 4.90 | 3.71 |

TABLE 1-continued

Composition of 'Canyon Mint' Oil from Test Plots Compared to commercial 'Black Mitcham' Peppermint Oil and Oil from 'Black Mitcham' Peppermint Grown in Test Plots located near Monmouth, Oregon.

| Essential Oil Components | Commercial 'Black Mitcham' 1/ | 2005 Test Plot 'Black Mitcham' 2/ | 2005 Test Plot 'Canyon Mint' 3/ |
|---|---|---|---|
| 1-menthone | 20.00 | 19.43 | 2.47 |
| Menthofuran | 4.35 | 4.23 | 44.02 |
| Iso-menthone | 3.19 | 3.14 | 0.58 |
| 1-menthyl acetate | 5.09 | 5.36 | 19.67 |
| Neo-menthol | 5.40 | 5.52 | 1.90 |
| B-caryophyllene | 0.83 | 0.85 | 1.60 |
| 1-menthol | 45.20 | 44.60 | 18.30 |
| Pulegone | 2.17 | 2.14 | <1.00 |
| Germacrene-D | 1.22 | 1.37 | <1.00 |

The numbers listed in the above table are percentages based upon the analysis of the respective mint oils by gas chromatography. The percentages are determined by calculation of the relative peak areas.

1/ Commercial oil sample typical of what is produced by peppermint producers.

2/ 'Black Mitcham' oil from a control plant in the 2005 seedling test plot.

3/ 'Canyon Mint' oil from a single plant harvest from the 2005 test plots.

TAXONOMIC DESCRIPTION OF 'CANYON MINT'

This new plant, under greenhouse and field growing conditions, is a bush type plant with lateral branches at each node of the main stems. The height of 'Canyon Mint' is slightly less than 'Black Mitcham' growing under similar conditions and will vary based on fertilizer, soil quality, and water application, amongst other known factors that affect growth patterns. 'Canyon Mint' is between 0.3 and 0.5 m at mid-stem in width and 0.5 to 0.65 m in height under greenhouse environment. Field grown 'Canyon Mint' has a width of 0.3 to 0.5 m and a height of 0.5 to 0.75 m. Secondary and tertiary branching occurs to form a compact growth habit. When 'Canyon Mint' is mature and ready for harvest, the main stem at mid-plant (approximately between the eleventh and twelfth node) is 3.9-4.2 mm in width. The secondary and tertiary branch stems are 1.5-2 mm and 1-2 mm in width, respectively. The length of secondary branches are 10-15 cm. The tertiary branches, when present, are up to 6 cm in length. The stems are square, glabrous, and a green color that matches Fifth Edition Royal Horticultural Society Colour Chart 143B Green Group.

Mature leaves at the bottom of the plant are ovate lanceolate as are leaves on secondary branch stems. Leaves on upper mature plants, both main and secondary stems, are more lanceolate (FIG. 3). The adaxial leaf surface is glabrous. The abaxial leaf surface is sub-glabrous with oil glands distributed across the surface. Mid-main stem leaf size at flowering is 28-32 mm in width and 58-65 mm in length. Leaf size on secondary branches at flowering is 16-20 mm in width and 28-32 mm in length. Leaf petioles on the main stem leaves are 10-14 mm in length while petioles on secondary branch stem leaves are 4-6 mm in length. Leaves on the mid-main stem and lower tend to be slightly lobed and denticulate while the leaves on the upper plant tend to be more dentate. The main stem leaves are toothed having from 6 to 10 teeth on each side. The adaxial leaf is dark green in color, ranging from Fifth Edition Royal Horticultural Society Colour Chart 137B to 137C in the green group classification. The color of the abaxial leaf surface is a green color that matches Fifth Edition Royal Horticultural Society Colour Chart 146A, Yellow Green Group. The leaf has 6-9 lateral veins, more or less in parallel off the main vein that runs from the petiole to the tip of the leaf. The veins are prominent in all leaves of 'Canyon Mint.'

The inflorescence is an inconspicuous raceme 7 to 10 cm in length spike, with capitate flowers developing at the nodes of raceme. The capitate flowers are 15-20 mm in width and 10-15 mm in length. The length of the inflorescence is influenced by environmental factors. The flowers consist of five petals fused into a two lipped corolla. The corolla is light in color ranging from Fifth Edition Royal Horticultural Society Colour Chart 84D in the Violet Group to Fifth Edition Royal Horticultural Society Colour Chart N155B in the White Group. The Calyx is generally yellow-green and is 143C Fifth Edition Royal Horticultural Society Colour Chart, Green Group. The gynoecium consists of a single pistil with two lobed stigma that is exserted. The androecium consists of four stamens, each with a distinct filament and anther.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosure as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust, and producing a unique essential oil.

* * * * *

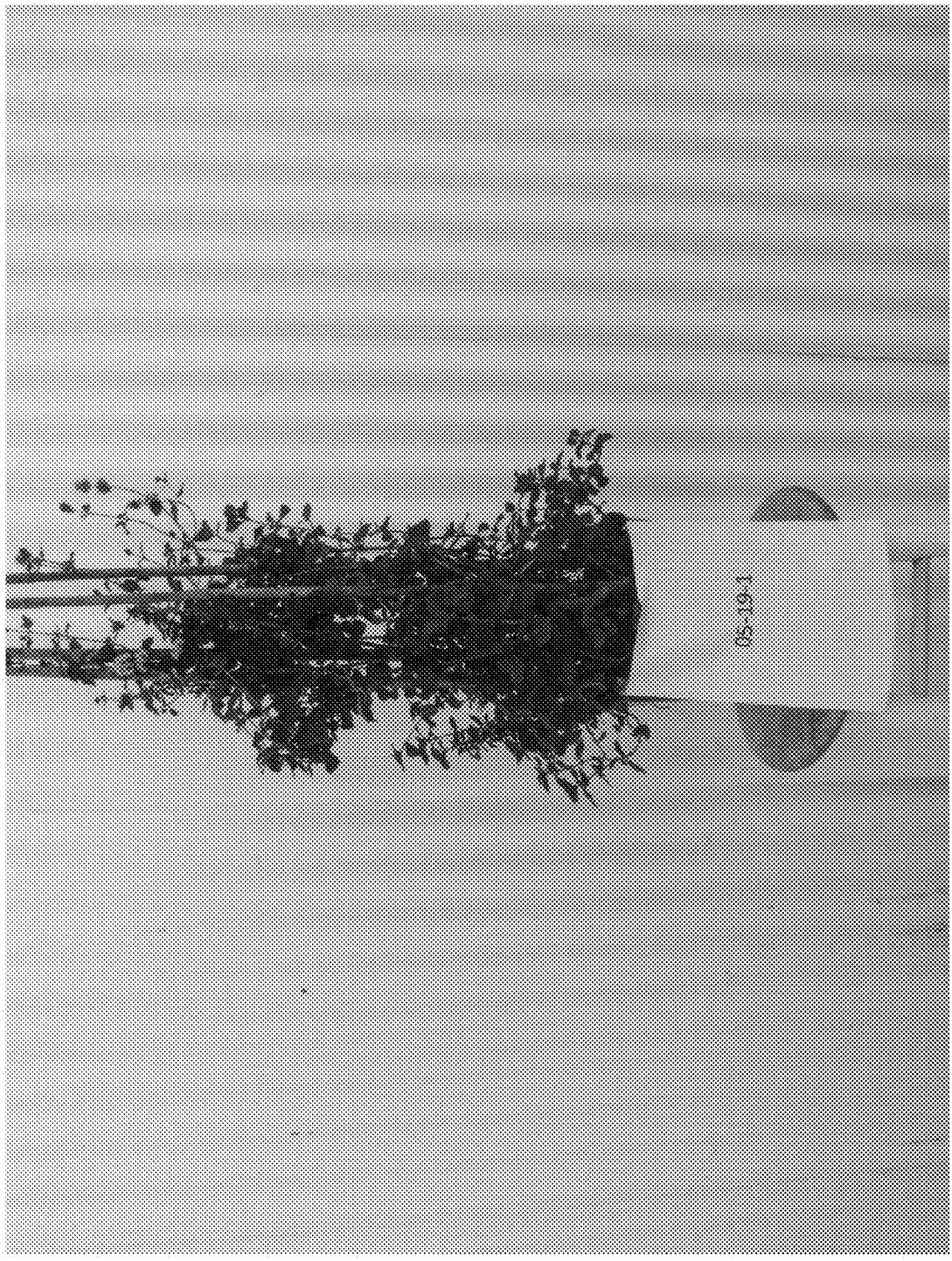
05-19-1

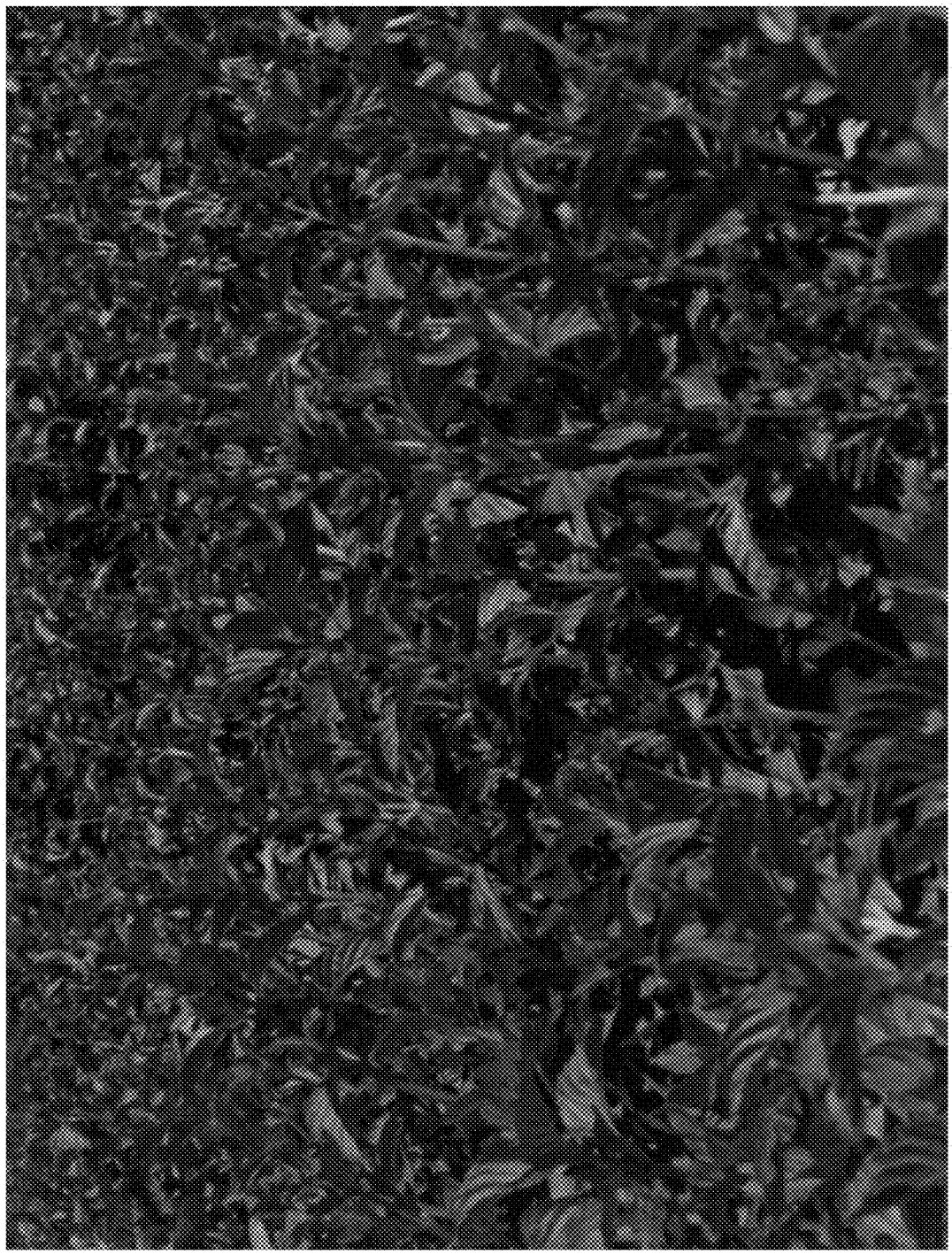

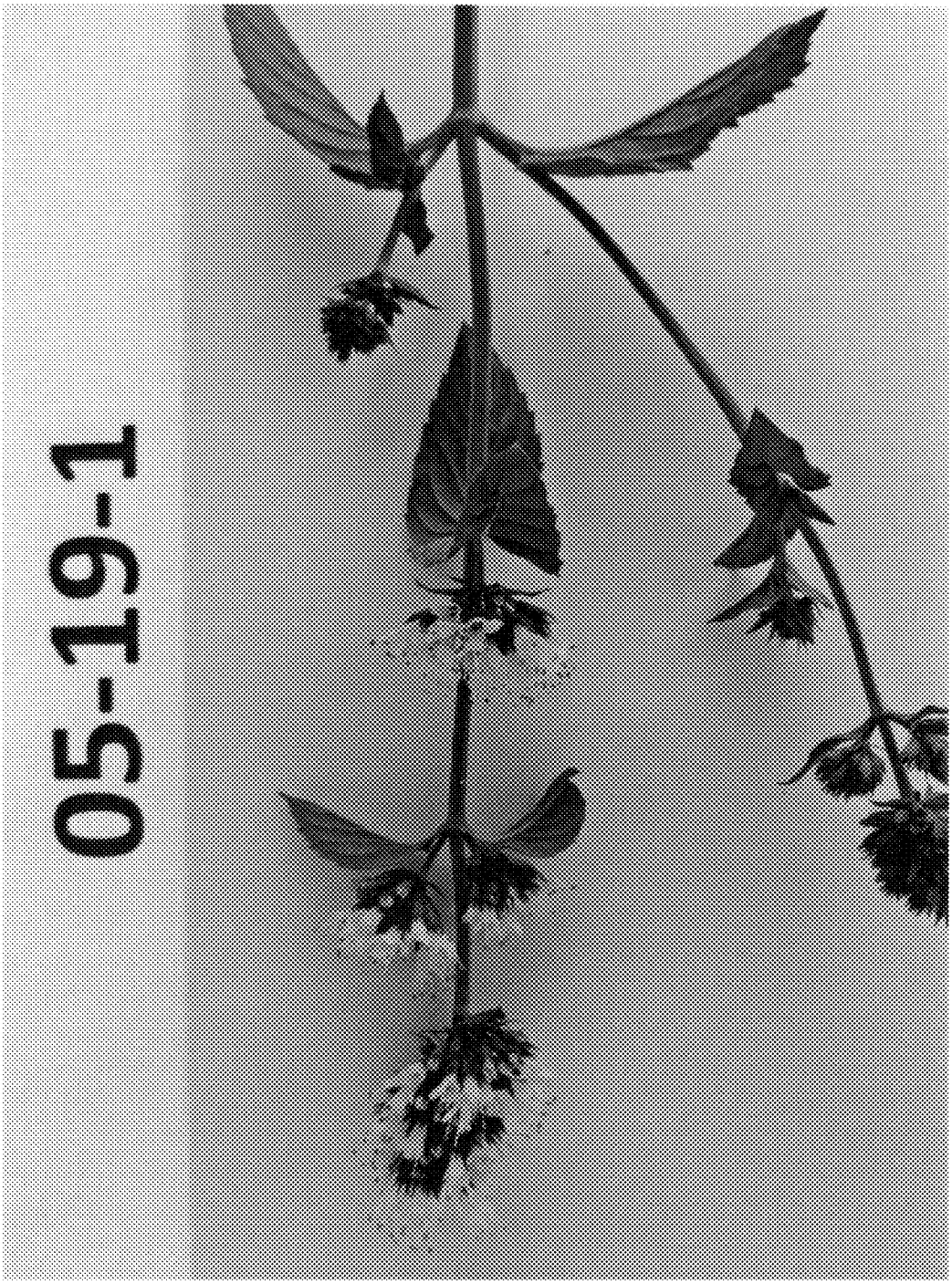
05-19-1
T-61T-50